United States Patent [19]

Rubic

[11] Patent Number: 4,776,852
[45] Date of Patent: Oct. 11, 1988

[54] ARTIFICIAL MUSCULOSKELETAL MECHANISM

[76] Inventor: Frank R. Bubic, 5140 MacDonald, apt. 1602, Montreal, Quebec, Canada H3X 3Z1

[21] Appl. No.: 934,485

[22] Filed: Nov. 24, 1986

[30] Foreign Application Priority Data

Dec. 11, 1985 [CA] Canada .................................. 497,386

[51] Int. Cl.⁴ .............................................. A61F 2/72
[52] U.S. Cl. ........................................... 623/26; 92/44
[58] Field of Search .......................... 623/14, 26, 16, 30, 623/40, 57, 59–62; 901/28, 22, 1; 92/44, 40, 36, 89–92, 35, 37, 39

[56] References Cited

U.S. PATENT DOCUMENTS

| | | | |
|---|---|---|---|
| 2,470,480 | 5/1949 | Fogg | 623/26 |
| 2,483,088 | 9/1949 | De Haven | 92/90 |
| 2,568,053 | 9/1951 | Certranis | 623/26 |
| 2,605,474 | 8/1952 | Oliver | 623/26 |
| 3,153,881 | 11/1964 | Baulard-Cogan | 623/26 X |
| 3,160,290 | 12/1964 | Wilson | 901/22 X |
| 3,638,536 | 5/1972 | Kleinwachter et al. | 623/26 X |
| 3,713,685 | 4/1973 | Ewing | 623/26 X |
| 3,751,733 | 8/1973 | Fletcher et al. | 623/24 |
| 3,799,159 | 6/1974 | Scott | 623/26 X |
| 3,967,809 | 7/1976 | Skartar | 92/92 X |
| 3,993,056 | 12/1976 | Rabischong et al. | 128/89 R |
| 3,995,324 | 6/1976 | Burch | 623/26 |
| 4,180,870 | 3/1980 | Radulovic et al. | 623/26 |

FOREIGN PATENT DOCUMENTS

| | | | |
|---|---|---|---|
| 316515 | 12/1919 | Fed. Rep. of Germany | 623/26 |
| 1148365 | 4/1969 | United Kingdom | 901/28 |

Primary Examiner—Richard J. Apley
Assistant Examiner—Howard Flaxman
Attorney, Agent, or Firm—Robic, Robic & Associates

[57] ABSTRACT

An artificial skeletal mechanism having a central rigid inverted T-shaped link and a pair of elastic tubular actuators on either side of the link, each actuator having an inner chamber for receiving a pressure fluid serving to pretension it. Each actuator has one end articulated to one end of the cross bar of the T so that they are antagonistically pretensioned. The artificial skeletal mechanism is intended to transform the contraction of one actuator, following extension of the other, into rotation of the link which is articulated at the free end of its long bar.

16 Claims, 3 Drawing Sheets

ARTIFICIAL MUSCULOSKELETAL MECHANISM

BACKGROUND OF THE INVENTION

1. Field of the invention

The present invention relates to an artificial musculoskeletal mechanism of the type using extensible and contractible liquidtight robotic actuators.

2. Description of the related art.

Considerations of economy and reliability suggest that the lifelike mechanical properties of actuating mechanisms in the future highly versatile, mobile, interactive and autonomous robotics should be preferably the inherent features of their design concepts rather than the operating features which have to be artificially simulated by some externally programed controls. Furthermore, the design and construction of robots suitable for labour intensive tasks is unattainable with existing mechanical hardware whenever the human-like strength, responsiveness to controls involving complex systems dynamics, versatility, energy efficiency, precision and weight limitations imposed by the mobility requirements are to be combined in one machine.

While the structural design of a live musculoskeletal system, particularly that of an appendicular skeleton, can be emulated by a mechanically equivalent articulated framework, the known types of machine elements do not offer satisfactory solutions for the construction of a complete artificial musculoskeletal mechanism which would have basic geometry and mechanically critical actuating features comparable to those of a living limb. Electromechanical solutions can produce mechanisms which meet typical configurations of live musculoskeletal systems, but recreating the lifelike dynamic responses is either impossible or costprohibitive. Fluid power actuators, although successful when applied in conventional machinery, do not offer satisfactory solutions for proposed lifelike mechanisms in robotics either, because of their rigidity, weight, complexities involved in simulating needed dynamic properties, internal friction aggravated by tight seals (particularly critical for the relatively slow, short, positioning motions against light loads when static friction caused <sticking> results in an erratic breakaway behaviour), absence of absolute liquidtightness due to unavoidable use of dynamic seals etc.

The robotic actuating mechanism proposed by the present invention possesses critical mechanical qualities of a real musculoskeletal system as explained hereafter; the construction of its actuators is absolutely liquidtight; it can be made by using the existing engineering materials and manufacturing techniques, and it can be used for construction of mobile industrial robots and motorized artificial limbs for the handicapped.

SUMMARY OF THE INVENTION

The present invention provides a new type of artificial skeletal mechanism, referred to hereafter as ASM, which is functionally equivalent to the living musculoskeletal mechanism in which each reversible motion of a long bone of a limb is generated essentially by the contraction of one of two mutually antagonistic living muscles. Each mechanically equivalent actuator in an ASM is, essentially, a longitudinally extensible tube prestressed at assembly so that it tends to contract and move a common T-shaped link, articulated at the base, in a direction which is opposite to the one in which the T-link would be moved by contraction of an antagonistic actuator. In this mechanism, one actuator is allowed to contract and do the work whenever its opposing actuator is lengthened by an application of internal pressure. Radial expansion of both actuators is substantially restricted by a suitable circumferential reinforcement inside the tube walls.

While the contracting actuator does the work, the extending contractor stores energy which remains available for a reverse motion. When an actuator tube is internally guided, so that it can withstand also an axial compression, higher pressures than those needed to overcome nominal tension at a given length may be applied so that such an actuator can, without loosing any of its contractile properties, contribute to the overall active torque and work output of the musculoskeletal mechanism even while the said actuator expands.

A circumferentially reinforced pressurized tube, made from either an elastic material or corrugated fabric, can withstand only those internal pressures whose total axial force is in equilibrium with the axial tube tension. As a result, no effective external actuating force can be generated by such devices in elongating mode, because any additional pressure beyond the above limit would convert them into externally compressed soft columns which immediately fail due to buckling of the tube walls. The radial component of the internal pressure does tend to maintain the round shape of the cross-section, but this action alone does not provide the overall structural stability of the flexible tube under compressive loads as proven experimentally during development work on this mechanism.

It is, therefore, one of the objects of the present invention to provide a spontaneously contractile actuator which can be also elongated and which does not collapse under compressive axial loads occurring either in operation due to higher than nominal pressure, or when an ASM at rest with its fluid supply lines closed for holding duty, is exposed to variable external loads in either direction. This feature of guided contractile actuator within an ASM improves also active regeneration of energy during deceleration of external loads by allowing an ASM to oppose torques which result in compressive loads on its actuators.

The principles applied in the conception of the ASM, according to the present invention, regarding the lifelike properties outlined above in the BACKGROUND OF THE INVENTION are as follows.

The mechanim rotates as a result of an unbalanced tension of one of its actuators, just as living musculoskeletal mechanism does.

The relationship between the torque of an ASM and its angle of rotation can be made similar to that of a living musculoskeletal mechanism because, in addition to a comparable kinematic concept, the maximum tensions of its actuators vary with length similarly to the tensions of living muscles; i.e. the tensions are greatest at maximum working lengths and they always decrease when lengths decrease. Furthermore, this invention provides the means for modification of force/extension relationships of ASM actuators to match closely those of the living muscles.

The contraction range of a real muscle is approximately the rest length +35% which falls very safely within allowable elongations of most neoprenes and even many butyl and GR-S rubber compounds, while natural rubber can exceed these elongations quite substantially.

An ASM operating pressure of 700–1000 kPA can be implemented with quite ordinary inexpensive standard materials and fabricating methods. Since the effective area corresponding to the inside diameter of a very strong ASM actuator will be at least 50% of its overall cross-section, the maximum live muscle tension of 350 kPa can be easily matched and if necessary exceeded, so that actuators of this mechanism will not have to be bulkier than the equivalent human muscles.

At any given angle, the ASM's torque is also a function of its angular velocity, just as for a live muscle mechanism.

The maximum torque is developed by both an ASM and a living limb under isometric conditions for any given angle.

At their maximum speeds, both types of mechanisms have a zero effective torque available for acting against external loads. The maximum ASM angular speed can be easily adjusted to either match or, if needed, exceed musculoskeletal standards.

The action of an ASM is controlled by applying and removing only one stimulus which is, in this case, fluid pressure. This feature equals the simplicity of control concept of a real musculoskeletal mechanism which also requires only one type of stimulus for its operation.

Both a live and the artificial musculoskeletal mechanism of the invention are based on a pair of antagonist muscles mounted on an articulated link which converts muscle extension and contraction into a rotary motion.

The ASM of the invention can maintain an isometric or produce an isotonic action like a live limb. They can act as prime movers as well as in a synergetic or stabilizing mode (holding duty) within a musculoskeletal robotic system just as live mechanisms do.

The basic compounded dynamic models of both types of mechanisms used in the invention have each at least three elements. Each has one contractile element which, when stimulated, tends to shorten the model. Each combination has one passive parallel elastic element which tends to restore rest length—or neutral position of the musculoskeletal mechanism.

Each compounded model has one series elastic element which brings about shock-absorbing qualities within mechanical concept of either natural or artificial skeletal mechanism. In the case of ASM, a series elstic element represents radial elastic deformation of the extensible tube which, although circumferentially reinforced, is made to allow also a limited radial expansion.

A compounded dynamic model of either live or artificial musculoskeletal mechanism referred to herein is the model which represents dynamic properties of one fictitious actuator which, contracting alone on one side of a T-link, would have in every respect the same actuating effects as the ones that two muscles or two ASM actuators have when acting on two opposite sides. Although the active contractile element of an ASM actuator is negative, i.e. direct effect of pressure application is extension of an ASM actuator while a stimulated live muscle contracts, the overall dynamic behaviour of an ASM results in the same compounded model as that of a live musculoskeletal mechanism.

The basic compounded model is the one in which only primary muscle responses are represented i.e. A. V. Hill's contractile, parallel elastic and serial elastic elements, while the viscous responses are neglected as secondary.

More advanced variations of the basic Hill's dynamic model of the real muscle do involve also two separate viscous elements—one associated with contractile and one with parallel elastic branch of the model. General compounded dynamic model of an ASM involves also viscous responses associated with both contractile and parallel elastic elements.

An ASM has also load retarding capabilities like a living limb, i.e. moving loads can be decelerated or their descent can be moderated.

The mechanical properties of both types of mechanisms can be expressed in an algebraic form for any defined type of dynamic performance.

In addition to their lifelike physical properties, ASMs provide also the following advantages:

(a) Liquidtightness: As a fluid powered mechanism, ASM is an absolutely liquidtight assembly, since all of its fluid carrying components are either permanently bonded together, or assembled without dynamic seals.

(b) Simplicity: The number of components of a basic ASM is very small when compared to that of existing mechanisms in robotics based on classic drives and transmissions.

(c) Economy: Predominant or exclusive use of molded elastomeric materials combined with absence of the need for close tolerances makes all ASM's components disposable since they are much less costly than high accuracy, predominantly metallic parts of conventional machinery.

(d) Uninhibited response: The shortest, the lightest and the slowest movements can be initiated without any <stick-friction> within ASM's actuators.

(e) No backlash: Nothing ever gets loose within a permanently prestressed ASM.

(f) No overstressing: A pressure relief in fluid supply system combined with ASM's own inherent limitation of the generated torque, excludes possibilities of a mechanical or structural damage due to overload.

(g) Stored energy within an ASM improves its responsiveness and, in case of a power supply failure, provides a possibility of executing a <hands-off> movement when necessary (e.g. moving a power tool handled by a robot away from the workpiece; providing a <dead-man> feature not normally available in robot with a classic drive which tends to <freeze> in situations in which a disabled person would collapse etc.)

(h) Energy regeneration: Within a network of ASM actuators, the energy is directly regenerative so that actuators involved in load retarding duties can save a substantial portion of the overall energy rate of consumption which is significant for autonomous machines.

(i) Low inertia: Direct generation of tensions and torques without high speed geared-down machinery provides low inertia mechanical response of an ASM.

(j) Low maintenance: An ASM can be made from disposable self-lubricating parts with zero maintenance requirements during service life.

(k) Force and motion feed back: By monitoring the pressure and flow in and out of one actuator per mechanism, a central control system can be informed about the loads, velocities, accelerations and consequently about forces and positions of the robot's links and end-effectors without a network of force and position sensors scattered throughout the entire machine. Vision guidance is needed only for final precision movements and not for primary planning and execution of the entire trajectories.

The contraction force of either ASM actuator for any length is given by the formula $$F = \int_o^e E_p de - pA + v_c\eta$$

where p is the pressure, A is the crossectional area corresponding to the inside diameter, e is the elongation, $E_p$ is the modulus of parallel elastic element, $v_c$ is the velocity of the contractile element and $\eta$ is the viscosity factor.

The axial contracting velocity of either ASM actuator is obtained from the formula $$V = -\frac{Q}{A} \pm v_s$$

where Q is the flow rate and $v_s$ is the velocity of the serial elastic element which is negative when the actuator's tension decreases, positive when it increases, and zero when the force is constant. With the force and velocity of actuators known, a control system can evaluate the ASM loads, displacements, power and work involved in any dynamic process.

(l) Artificial limbs: The strength and lifelike flexibility of ASMs make them more suitable for design of advanced motorized prostheses than conventional machinery is.

(m) Better than lifelike performance: Without loosing any of the complex critical live mechanical properties, an ASM can be made to exceed the real musculoskeletal performance in strength, speed and precision in addition to being impervious to the human-like physiological and psychological fatigue.

Two ASMs with a common vertical section for their T-links, acting in two mutually perpendicular planes and having all ball-joint connections, can provide two degrees of freedom of a robotic link. In some configurations, ASMs can provide also a limited amount of link rotation around its longitudinal axis.

More specifically, the ASM of the invention essentially comprises: a central rigid link having the general shape of an inverted T with a long bar and a cross bar; a pair of elastic tubular actuators, each actuator defining an inner fluid pressure chamber; wherein the actuators are formed with fluid flow passages leading into the pressure chambers for feeding controllable pressure fluid thereinto capable of stretching the elastic actuators and capable of controlling the axial tension thereof, and first and second articulation means respectively mounting one end of the actuators to one of the free ends of the cross bar.

One of the actuators preferably comprises: a circumferentially reinforced axially extensible tube; rigid plugs secured to the ends of the tube, one of the plugs having a circumferentially recessed end located inside the chamber of the one actuator, the recessed end having a diameter smaller than the inner diameter of the tube; and a rigid tubular guide which provides capability of resisting compressive loads in the chamber of the one actuator, the guide having one end secured to the other of the plugs and having the other end slidably fitted in the circumferentially recessed end.

The actuator may also be of the form comprising: a circumferentially reinforced axially extensible tube; rigid plugs secured to the ends of the tube, one of the plugs having an extension outwardly of the chamber of the one of the actuators; elastic walls, over the extensible tube, the elastic walls having one end secured to the other of the rigid plugs and the other end of the elastic walls being slidable over the plug extension, and concentric rigid rings holding the elastic walls and tube spaced apart from one another.

The geometry of an ASM may be asymmetrical and antagonist actuators can be of dfferent types, sizes and lengths to suit application.

BRIEF DESCRIPTION OF THE DRAWING

A description of a preferred embodiment of the invention now follows having reference to the appended drawing wherein.

DESCRIPTION OF THE PREFERRED EMBODIMENT

Figure 1:
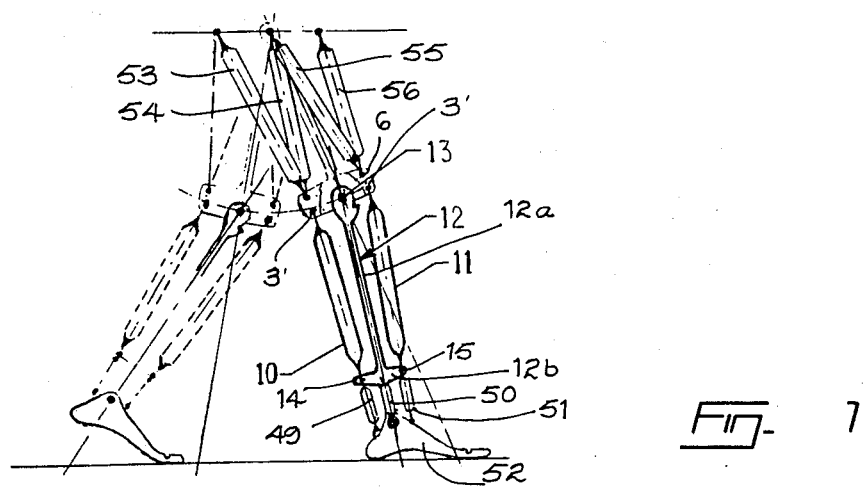
FIG. 1 is a diagram illustrating an artificial limb assembly and showing two pretensioned actuators causing rotation of an articulated T-shaped link.

The artificial limb assembly of FIG. 1 shows an ASM made according to the invention which includes an inverted T-shaped rigid link 12 having a long bar 12a and a cross bar 12b. The free end of the long bar 12a has an articulated joint allowing rotation of the link 12 about an axis 13 transverse thereto. Two robotic actuators 10 and 11 have a lower end mounted at the free ends of the cross bar 12b for rotation about respective axes 14 and 15 parallel to axis 13. In the construction shown, the actuators 10 and 11 are able to cause oscillation of the link 12 about its articulation axis 13 whenever the tension in either one of the actuators overcomes the combined action of its own antagonistic load and of any external load applied thereto.

Figure 2:
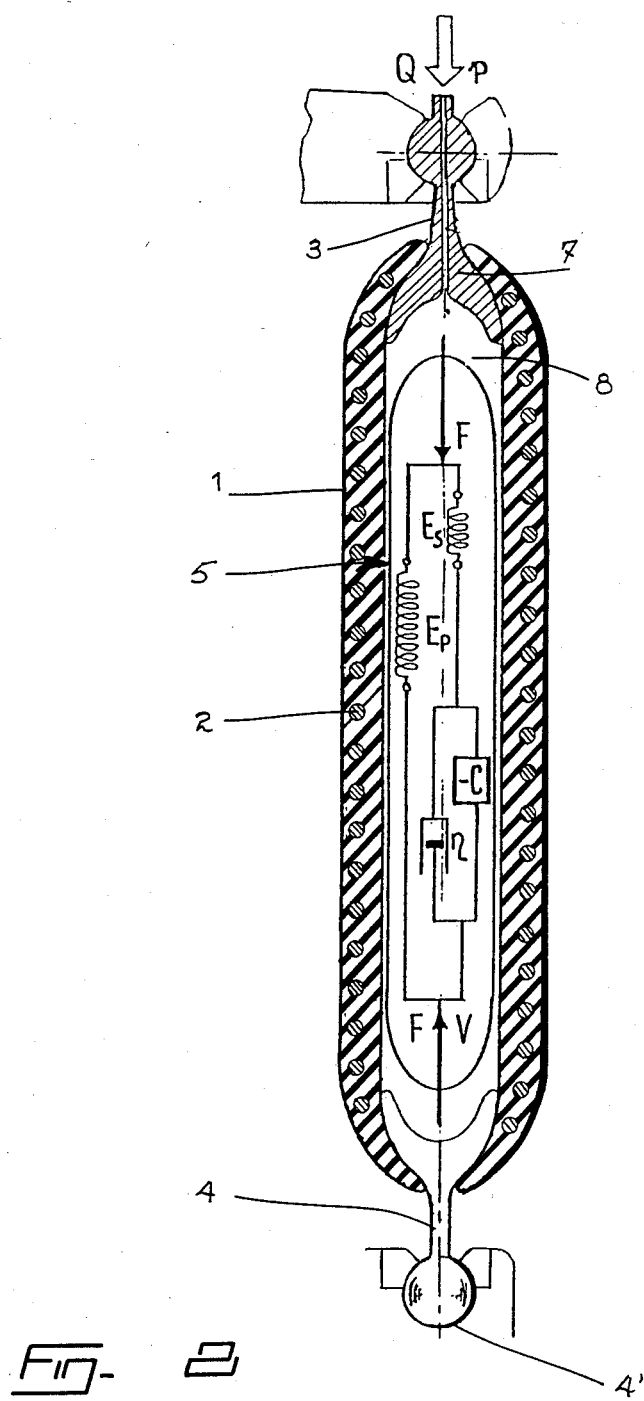
FIG. 2 is a diagrammatic longitudinal cross-sectional view intended to illustrate the basic concept of an ASM actuator, according to the invention, and including its load diagram.

Basically, as shown in FIG. 2, a pretensioned contractible actuator such as 10 or 11 of FIG. 1 comprises an outer elastic tube 1 that can be molded or made of wrapped construction or as a corrugated fabric. The two ends of tube 1 are turned inward and are permanently bonded, in any known manner as by means of an adhesive material, onto hard plastic or metal plugs 3 and 4 provided with connecting heads 3' and 4' suitably shaped for ball joint connection, as shown. They may however be shaped for other types of articulated joint connections such as a pin connection. Connecting heads 3' of connectors 10 and 11 are shown mounted, in FIG. 1, for articulation on a transverse support plate 6 which is part of a known limb assembly of which the ASM of the invention is an improved component. The articulation axes of the plug heads 3' and of the joint 13 are parallel.

Embedded by molding in the wall of the elastic tube 1, or otherwise secured to it, is a circumferential reinforcement 2 intended to prevent undue radial expansion of tube 1. It can be a coil or a series of concentric tough elastomer or metal rings having a round, oval or flattened cross-section. Tube 1 thus remains elastic and can expand axially.

Plug 3 and its connecting head 3' are formed with a passage 7 allowing injection and removal of pressure fluid in and out of the chamber 8 of actuator tube 1.

A spacer 5, made of hard coated structural foam or as a hollow plastic or metal shell, is housed freely in the chamber 8 and serves to restrict the required quantity of pressure fluid in chamber 8 to the minimum required amount. It also serves to establish the minimum length of the actuator tube 1 when contracted.

The mechanical properties of this contractible and extensible device 1 to 8, in FIG. 2, are represented by the diagram of its dynamic model where F is the overall actuating tension, V is the overall contracting velocity, $E_p$ is the parallel elastic element representing the axial elastic response of tube 1, $E_s$ is a series elastic element representing the axial component of the actuator responses resulting from radial elastic deformation of tube 1, $\eta$ is a viscous element representing the resistance of fluid while being injected in or removed out of the chamber 8, and -C is an expanding element whose force is the product of the fluid supply pressure p and the inside area of tube cross-section A and whose expanding velocity is the quotient of the flow rate Q and the area A.

Figure 3:
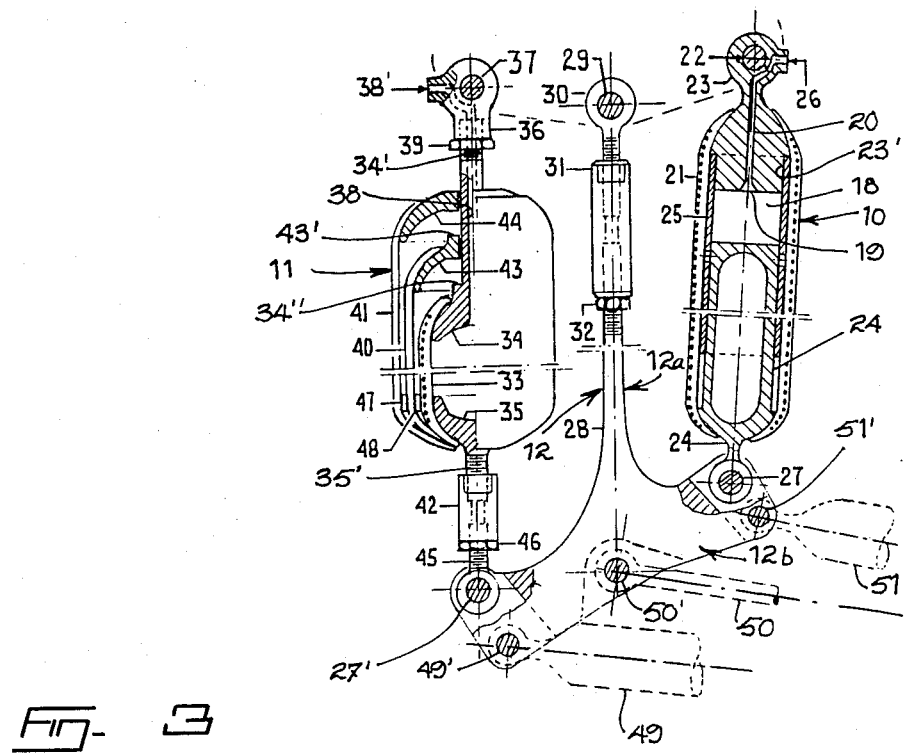
FIG. 3 is a side elevation view, partly in cross-section, showing an ASM constructed according to the teaching of the present invention.

In FIG. 3, an ASM made according to this invention is shown which includes the guided robotic actuator 10 of FIG. 1 having an elastic tube 21 of which the ends are provided with connecting plugs 23 and 24 articulated around pivot pins 22 and 27, the latter being further mounted at one end of the cross bar 12b of link 12. The connecting plug 23 has a pressure fluid passage 20 having an outer orifice 26 and an inner orifice 19 opening into a chamber 18 of the actuator 10. The end of plug 23 which is within the chamber 18 is formed with a circumferential recess 23' into which one end of a tubular guide 25 is firmly secured. The inward end of the other plug 24 is likewise formed with a circumferential recess 24' onto which the lower end of the tubular guide 25 loosely fits. This arrangement of the tubular guide 25 and plugs 23 and 24 thus enables proper guiding of the actuator elastic tube 21 during contraction and allows it also to withstand compressive loads since a flexible tube and column of fluid alone buckle under axial compression. The tubular guide 25 may be made of metal or other resistive material.

The long bar 12a of the link comprises a bar length 28 having a threaded end on which is screwed a length-adjusting take-up sleeve 31, with jam nut 32, at the other end of which sleeve is screwed an eye-bolt connector 30 pivoted to a pin 29 corresponding to the articulated joint 13 of FIG. 1.

The other robotic actuator 11 of the ASM shown at the left in FIG. 3 has a contractible and extensible liquidtight tube 33 similar in construction to the axially elastic tubes 1 of FIG. 2 and 21 of the right robotic actuator 10 of FIG. 3. It is likewise sealed at its ends with plugs 34 and 35. The connecting head of plug 35 is threaded at 35' for the mounting of a length-adjusting take-up sleeve 42 into the other end of which is likewise screwed an eye connector 45 pivoted on a suitable pin 27' provided at the leftward free end of the cross bar 12b of the link 12. A jam nut 46 holds the sleeve 42 in secured position relative to end plug 35 and link 12.

The other plug 34 of actuator 11 has a threaded end 34' at the end of an elongated extension. An eye-connector 36, pivoted on a pin 37, is screwed over the threaded end 34'. The position of the pin 37 with respect to the threaded end 34' is ensured by a jam nut 39. Pressure fluid is injected into or removed from the chamber of elastic tube 33 by means of a passage 38—38' of the end plug 34 and eye-connector 36, as shown.

The take-up sleeve arrangements 31 at the free end of link 12 and 42 at the lower end of left actuator 10 provide for the adjustment of the working length and rest position of the link 12.

Actuator 11 is further provided with two additional concentric elastic tubes 40 and 41, also concentric to elastic tube 33. Tubes 40 and 41 need not however be reinforced as is tube 33. The lower ends of tubes 40 and 41 are secured to the lower end of the tube 33, as shown, and spacer rings 47 and 48 keep tubes 33, 40 and 41 apart. The upper ends of tubes 40 and 41 are respectively provided with collars 43 and 44 solidly bonded thereto but slidable along the outer surface of the head of connecting plug 34, more precisely along its outward extension which terminates into the threaded end 34'.

Thus, after tube 33 has extended a predetermined length e1 (see FIG. 4), a shoulder 34" thereof comes in contact with collar 43. Tube 40 starts to elongate whenever the elongation of tube 33 exceeds e1. Tube 41 starts to elongate when the extension of tube 33 reaches a value e2 and a shoulder 43' of collar 43 comes in contact with collar 44.

Figure 4:
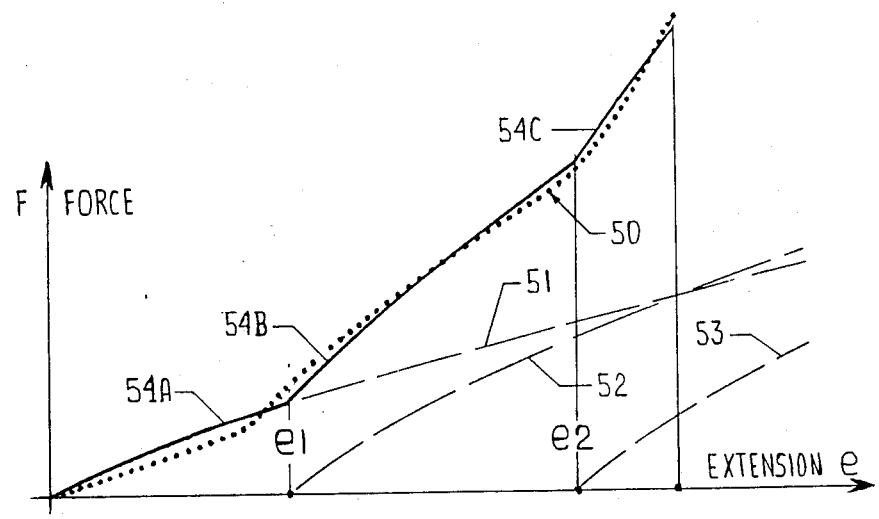
FIG. 4 is a curve diagram illustrating the force/extension relationship of a particular type of actuator in an ASM made according to the invention.

The curves in the diagram of FIG. 4 illustrate the behavior of a robotic actuator, such as that shown in FIG. 3, having several extensible tubes 33, 40 and 41.

Referring now to FIG. 4, dotted line 50 represents an assumed desirable force/extension function for an ASM robotic actuator needed to obtain a compounded dynamic model of an entire artificial musculoskeletal mechanism which responds in exactly the same way as does an equivalent live one. The curves 51, 52 and 53 represent respectively the force/extension relationships for tubes 33, 40 and 41. When forces given by 52 and 53 are added to those given by 51, starting at corresponding extensions e1 and e2, the curve made-up of sections 54A, 54B and 54C is much closer to the desired function 50 than any one single elastomeric force/extension curve with continuously negative second derivative could ever be. The degree of desired refinement and complexity of the required force/extension relationship of the compounded dynamic model of the entire mechanism dictates the number of separate tubes that are to be used.

Referring back to FIG. 1, the ASM of the invention may be used, for instance, on a robotic limb such as the leg assembly shown although it may also serve on other robotic assemblies as will readily be gathered by those skilled in the art.

Thus, with reference to FIGS. 1 and 3, the base or cross bar 12b of the link 12 is shown connected to a robotic foot section 52 by means of articulation members 49, 50 and 51 and corresponding pins 49', 50' and 51', while other articulation members 53 to 56 have a lower end articulated to the support plate 6 mentioned above. In the example of FIG. 1, the cross bar 12b of the link 12 is perpendicular to the long bar 12a while in that of FIG. 3, the cross bar 12b is inclined with respect to the long bar 12a, the degree of inclination being determined by the use contemplated. All articulation pins 22, 29, 37 - 27, 27' and 49', 50' and 51' pivot about parallel axes.

I claim:
1. An artificial skeletal mechanism comprising:
a support plate;

a central rigid link having the general shape of an inverted T with a long bar and a cross bar;

a pair of pre-stretched elastic tubular actuators, each actuator defining an inner fluid pressure chamber and being formed with a fluid flow passage leading into said inner pressure chamber for feeding controllable pressure fluid thereiento in order to stretch said elastic actuator and control the axial tension thereof, each of said actuators including means for altering the force produced by said actuators as a function of extension, wherein said actuators produces a force-extension curve substantially identical to that produced by an actual muscle, first and second articulation means respectively mounting one end of said actuators to one of the free ends of said cross bar; and third, fourth and fifth articulation means respectively mounting the free end of said long bar and the other ends of said actuators to said support plate, said articulation means allowing articulation of said actuators and link about parallel axes.

2. A mechanism as claimed in claim 1, wherein at least one of said actuators comprises:

a circumferentially reinforced axially extensible tube made of elastic material, said tube forming said force altering means,;

rigid plugs secured to the ends of said tube, one of said plugs having a circumferentially recessed end located inside said chamber of said one actuator, said recessed end having a diameter smaller than the inner diameter of said tube; and a rigid tubular guide which provides capability of resisting compressive loads in said chamber of said one actuator, said guide having one end secured to the other of said plugs and having the other end slidably fitted in said circumferentially recessed end.

3. A mechanism as claimed in claim 2, wherein the fluid flow passage of said one actuator extends through the other of said plugs.

4. A mechanism as claimed in claim 1, further including first mechanical means between said link and said third articulation means for regulating the tension in said actuators, and second mechanical means between one of said actuators and at least one of the articulation means thereof for adjusting the angular position of said link and of said actuators with respect to said support plate.

5. A mechanism as claimed in claim 4, wherein said first and second mechanical means are adjustable sleeve nut means.

6. A mechanism as claimed in claim 1, wherein at least one of said actuators comprises:

a circumferentially reinforced axially extensible tube made of elastic material;

rigid plugs secured to the ends of said tube, one of said plugs having extension outwardly of said chamber of said one actuator;

elastic wall, over said extensible tube, said elastic walls having one end secured to the other of said rigid plugs and the other end of said elastic walls being slidable over said plug extension, and concentric rigid rings holding said elastic walls and tube spaced apart from one another, wherein said extensible tube and said elastic walls from said force altering means.

7. A mechanism as claimed in claim 6, wherein the other of said actuators comprises:

a circumferentially reinforced axially extensible tube made of elastic material, said tube forming said force altering means;

rigid plugs secured to the ends of said tube, one of said plugs having a circumferentially recessed end located inside said chamber of said other actuator, said recessed end having a diameter smaller than the inner diameter smaller than the inner diameter of said tube; and a rigid rubular guide which provides capability of resisting compressive loads in said chamber of said other actuator, said guide having one end secured to the other of said plugs and having the other end slidably fitted in said circumferentially recessed end.

8. A mechanism as claimed in claim 6, wherein a shoulder is formed at the end of the plug extension of said one actuator away from the free end of said plug extension, and further comprising: collars around said other ends of said elastic walls slidable over said plug extension, said sliding collars being spaced from one another for successive engagement as said axially extensible tube expands and said shoulder butts against a first one of said collars.

9. A mechanism as claimed in claim 7, wherein a shoulder is formed at the end of the plug extension of said one actuator away from the free end of said plug extension, and further comprising: collars around said other ends of said elastic walls slidable over said plug extension, said sliding collars being spaced from one another for successive engagement as said axially extensible tube expands and said shoulder butts against a first one of said collars.

10. A mechanism as claimed in claim 8, including first mechanical means between said link and said third articulation means for regulating the tension in said actuators, and second mechanical means between one of said actuators and the articulation means thereof for adjusting the angular position of said link and of said actuators with respect to said support plate.

11. A mechanism as claimed in claim 6, wherein the fluid flow passage of said one actuator is formed through said plug extension.

12. A mechanism as claimed in claim 9, wherein the fluid flow passage of said other of said actuators is formed through said plug extension.

13. A mechanism as claimed in claim 6, further comprising articulation means at the center and at the ends of said link cross bar for the mounting of articulation members of another robotic link assembly.

14. A mechanism as claimed in claim 7, further comprising an elastic wall over the extensible tube of said other actuator.

15. A mechanism as claimed in claim 1, wherein at least one of said actuators comprises:

a circumferentially reinforced axially extensible tube made of elastic material, said tube forming said force altering means, rigid plugs secured to the ends of said tube; and a rigid spacer freely housed in the chamber of said one actuator to establish a minimum length to the extensible tube of said one actuator when contracted.

16. A mechanism as claimed in claim 6, further comprising a rigid spacer freely housed in the chamber of said at least one actuator to establish a minimum length to the extensible tube of said at least one actuator when contracted.

* * * * *